United States Patent
Brown

(10) Patent No.: US 6,720,773 B2
(45) Date of Patent: Apr. 13, 2004

(54) 4-ELECTRODE CONDUCTIVITY SENSOR WITH ZERO EXTERNAL FIELD

(76) Inventor: Neil L. Brown, 195 Falmouth Rd., Mashpee, MA (US) 02649

( * ) Notice: Subject to any disclaimer, the term of this patent is extended or adjusted under 35 U.S.C. 154(b) by 39 days.

(21) Appl. No.: 10/229,260

(22) Filed: Aug. 26, 2002

(65) Prior Publication Data

US 2004/0036476 A1 Feb. 26, 2004

(51) Int. Cl.[7] .............................................. G01N 27/02
(52) U.S. Cl. ........................ 324/449; 324/444; 324/446; 324/439
(58) Field of Search ................................. 324/449, 446, 324/444, 450, 439, 698

(56) References Cited

U.S. PATENT DOCUMENTS 4,019,134 A * 4/1977 Hogg ........................ 324/71.1

* cited by examiner

Primary Examiner—N. Le
Assistant Examiner—John Teresinski
(74) Attorney, Agent, or Firm—Lee & Hollander

(57) ABSTRACT

A conductivity sensor configuration which has essentially no external electrical field so that the calibration of the sensor is not affected by the existence of nearby external objects or fouling on the exterior parts of the sensor. Additionally, the sensor is relatively insensitive to electrode fouling or electrode polarization. The sensor includes a tube through which the liquid to be measured flows. An inner electrode plate extends partially along the length of the tube dividing the central portion of the tube into two sections. Two inner electrodes are located on the inner wall, one on each side, and two outer electrodes are located on the inside of the tube opposite the inner electrodes.

19 Claims, 3 Drawing Sheets

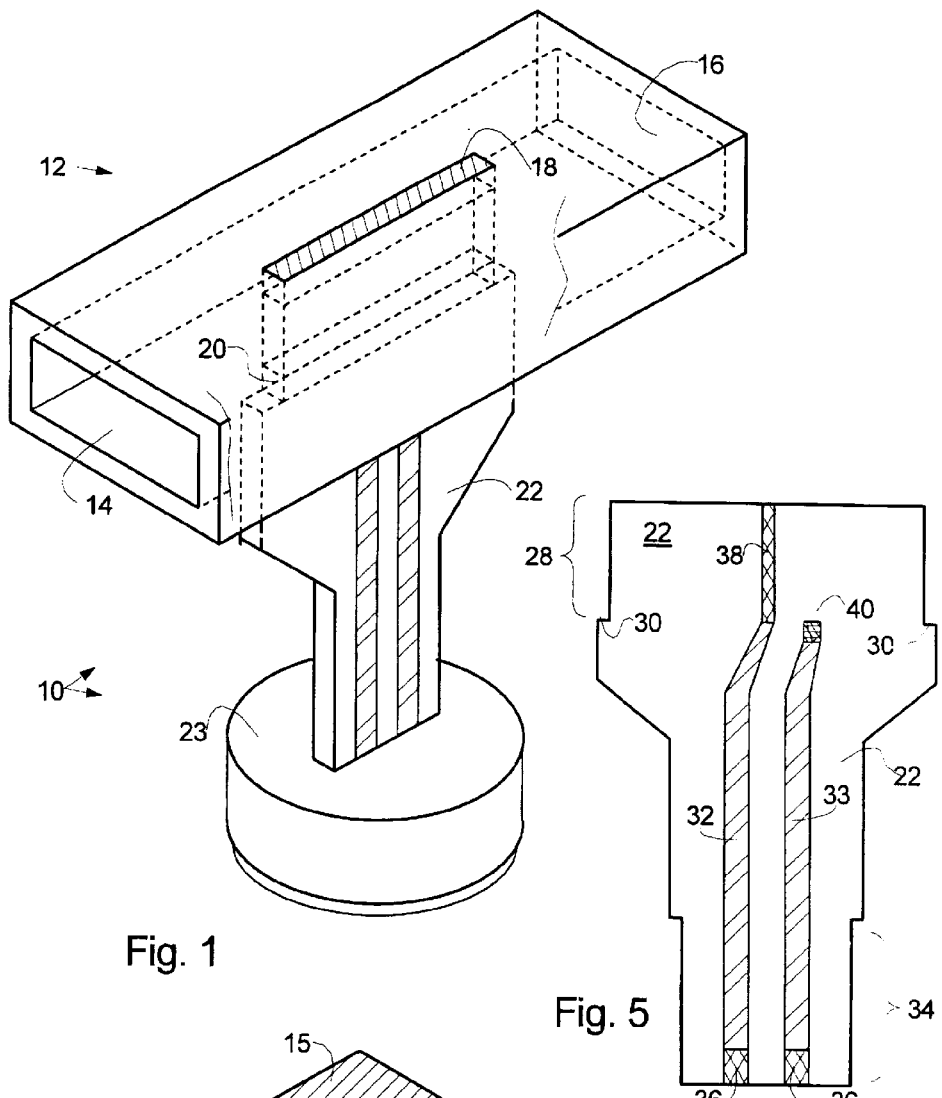
Fig. 1
Fig. 5
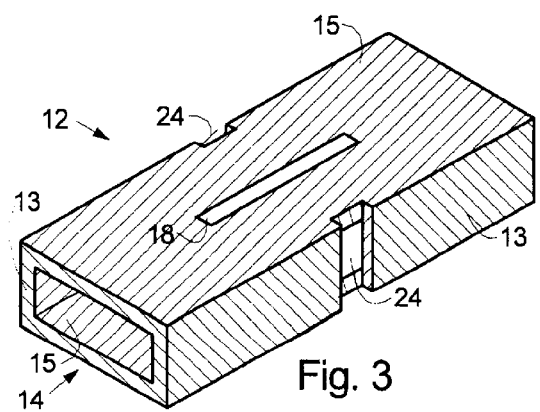
Fig. 3
Fig. 4

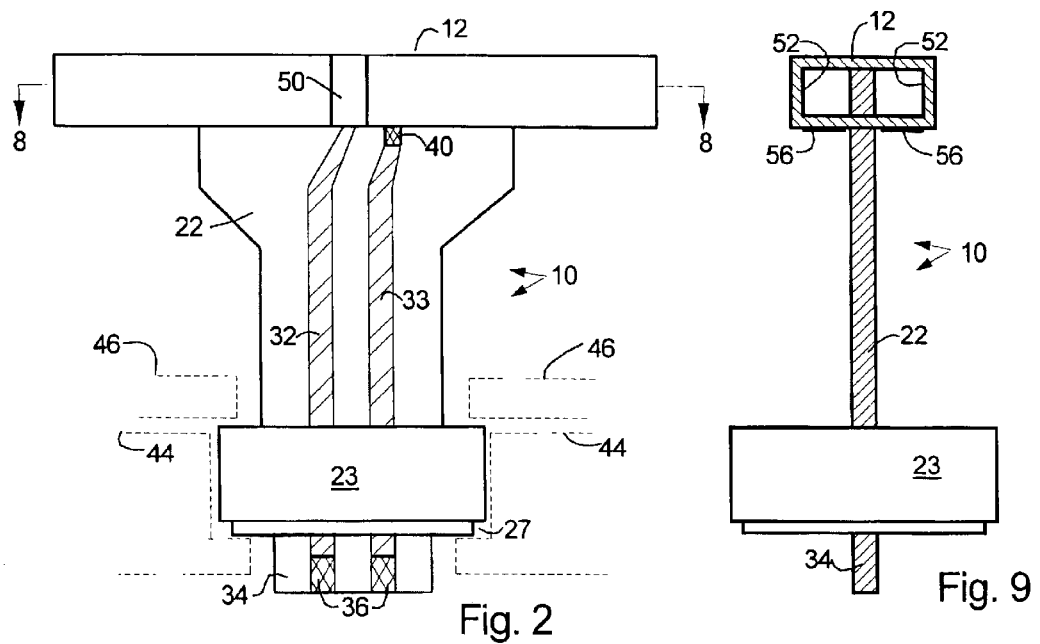
Fig. 2
Fig. 9
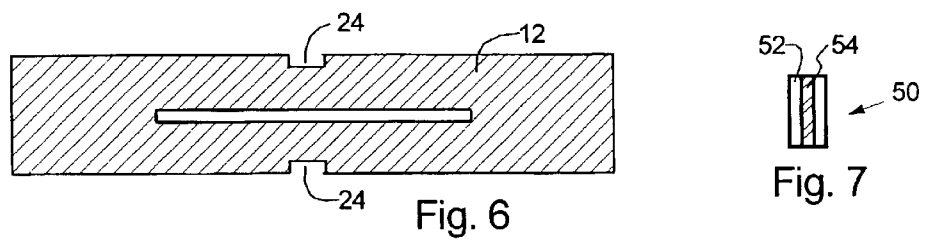
Fig. 6
Fig. 7
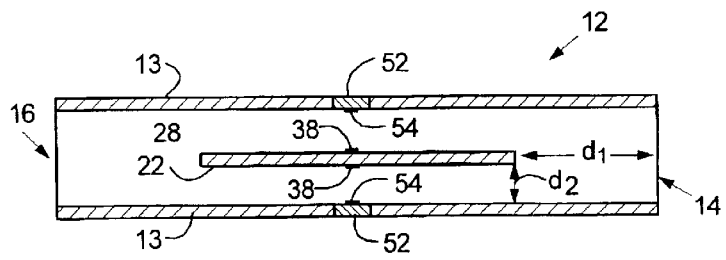
Fig. 8

4-ELECTRODE CONDUCTIVITY SENSOR WITH ZERO EXTERNAL FIELD

FIELD OF THE INVENTION

This invention is related to electrical conductivity measuring devices, and in particular to conductivity measurement of fluids.

BACKGROUND OF THE INVENTION

Industrial control systems and oceanographic studies frequently require the measurement of the electrical conductivity of a fluid, such as seawater. Several different types of conductivity sensors and systems have been developed to meet these requirements. The physical design of sensors for such measurements has proved to be challenging. Especially in ocean environments, the conditions that are present result in inevitable fouling of the sensor. Under extreme conditions, sensors may become so inaccurate or inoperable that they need to be replaced. Accordingly, a sensor design which minimizes the effects of such fouling on the accuracy of the measurement is very important.

The sensitivity, or calibration factor for conventional conductivity sensors is affected by the presence of nearby objects. Therefore, it may be necessary to calibrate them in the configuration in which they will be deployed, for example a deep-ocean sensor would have to be calibrated while mounted on the large pressure housing to which it is attached. This makes the calibration much more burdensome and interferes with easy replacement of malfunctioning sensors in the field.

SUMMARY OF THE INVENTION

The present invention includes a unique conductivity sensor configuration which has essentially no external electrical field. As a result, the calibration of the sensor is not affected by the existence of nearby external objects. Additionally, the sensor is relatively insensitive to electrode fouling or electrode polarization.

The sensor includes a tube through which the liquid to be measured may flow. An inner electrode plate extends partially along the length of the tube dividing the central portion of the tube into two sections. Two inner electrodes are located in the middle of the inner wall, one on each side, and two outer electrodes are located on the inside of the tube directly opposite the inner electrodes.

The electrode plate extends downwardly through a slot in the tube and further through a mounting base section. The base may be secured in a pressure housing, with the sensor being supported above the housing by the electrode plate. Conductive stripes on the surface of the electrode plate provide for electrical connection from within the housing to the inner and outer electrodes. Except for the electrodes, the conductive stripes are insulated from the conductive fluid, such as by an insulating coating applied over the stripes.

DESCRIPTION OF THE DRAWINGS

The advantages and operation of the present invention are more fully set forth in the following description of the preferred embodiment and by reference to the drawings, of which:

FIG. 1 is a perspective view of the assembled conductivity sensor of the present invention;

FIG. 2 is a side view of the sensor;

FIG. 3 is a view of the measurement head of the sensor;

FIG. 4 is a top view of the base;

FIG. 5 is a side view of the electrode plate;

FIG. 6 is a top view of the measurement head;

FIG. 7 shows an outer electrode assembly;

FIG. 8 Is a cross-sectional view of the assembled measurement head along the plane shown in FIG. 2;

FIG. 9 is an end view of the conductivity sensor;

DESCRIPTION OF THE PREFERRED EMBODIMENT

Figure 10:
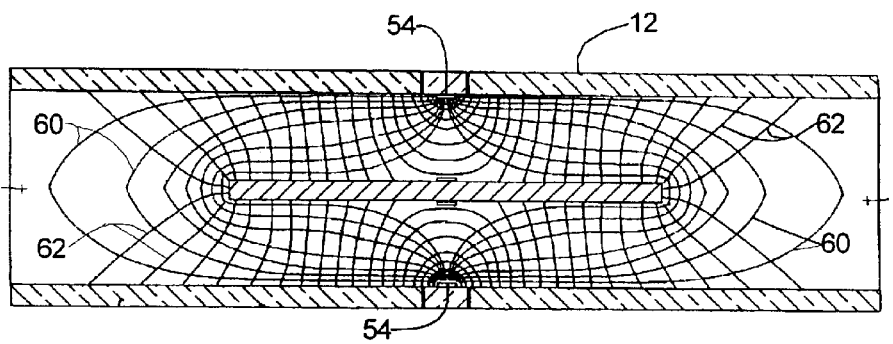
FIG. 10 shows current and field lines when the inner electrodes are used for voltage measurement.

The conductivity sensor of the present invention is a four-terminal, contacting sensor in which a current from two terminals is made to flow through the liquid and the resulting voltage across the other two terminals is measured. By calibrating such a device, a calibration factor may be determined which relates the measured voltage to the conductivity of the fluid. Such devices are known in the art.

Unlike prior art sensors, the calibration factor of the present invention is not affected by nearby objects or by fouling of the exterior surfaces. Further, the internal electrical fields are such that it is relatively insensitive to electrode fouling and to electrode polarization effects.

A preferred embodiment of the present invention is the conductivity sensor 10 shown assembled in FIGS. 1 and 2. FIG. 1 is a perspective view, and FIG. 2 is a side view. The sensor 10 includes a measuring head 12 in the form of a tube of rectangular cross-section and having open ends 14 and 16.

FIG. 3 shows measuring head 12 in isolation. It is comprised of side walls 13 and top and bottom walls 15. The side walls 13 include two slots 24 formed in each side of the rectangular tube and communicating with the interior. These slots are for the outer electrode assemblies, as explained in more detail below.

The measuring head 12 is mounted on and supported by an electrode plate 22 which extends through two rectangular slots 18 and 20 in the top and bottom walls 15 of the measuring head. The slots are located halfway along both the width and length of the measuring head. When the electrode plate 22 is inserted into the slots, its top section 28 extends longitudinally along the inside of the measuring head 12 and divides the inside of the tube into two sections.

The bottom of electrode plate 22 extends through and is secured by a base 23. As shown more clearly in the top view of base 23 in FIG. 4, a slot 25 extends through the base and receives the lower section 34 of the electrode plate.

The electrode plate 22 is shown in side view in FIG. 5. The upper section 28 extends into the measuring head through slots 18 and 20. Typically shoulders 30 are formed at the bottom of upper section 28 of plate 22 to securely position and locate the measuring head thereon.

It should be appreciated that when the terms "upper," "lower," and the like are used in this description of the preferred embodiment, these terms refer to the invention as illustrated in the accompanying figures. When actually deployed in an ocean or other environment, the device may be in any orientation.

The electrode plate includes four conductive stripes, two on each side, all of which are insulated from the conductive fluid, such as by an insulating coating or other suitable means. FIG. 5 shows two of the stripes 32 and 33. Two identical stripes, not shown in FIG. 5, are formed on the opposite side of electrode plate 22. An inner electrode 38 is formed as an extension of the conductive stripe 32 and is in the center of the upper section 28. The other stripe 33 terminates in a connection pad 40 which is located just below measuring head 12 when the sensor is assembled. This connection pad is used to provide electrical connection to the outer electrodes, as described below.

The measuring head 12 and electrode plate 22 should be constructed from a material which is an insulator and has a high mechanical rigidity. Ceramic is one material that is suitable although other materials may be used. In the described embodiment, the thickness of the walls of measuring head 12 and electrode plate 22 is about one to two millimeters. The electrodes and conductive stripes may be applied to the surface of the ceramic by sputtering, evaporation, silk screening, or other suitable operation. The different parts of sensor 10 may be secured in place after being assembled by fused glass or other suitable adhesive, such as epoxy resin.

Each of the stripes terminates at their lower end in a connection pad 36. Referring to FIG. 2, it can be seen that the lower section 34 of the electrode plate extends through the slot in the base so that the connection pads 36 are accessible at the underside of the base 23.

When used in an ocean or other high pressure environment, the conductivity sensor 10 is typically mounted on a pressure vessel or other instrument housing, which would house the measurement electronics for the sensor and possibly other instruments. FIG. 2 illustrates this, with the base 23 being mounted in a recess in a pressure housing wall, denoted by dashed lines 44. The base is held in place by a retaining ring 46 or similar means. A groove 27 may be provided around the bottom of base 23 for an O-ring gasket.

FIG. 6 is a top view of the measuring head 12 showing slots 24 where the two outer electrodes are located. FIG. 7 shows the structure of each of the two outer electrode assemblies 50. Each assembly includes a mounting plate 52 on which is formed a metallic electrode 54. The mounting plate 52 is preferably made of the same material as the measuring head tube 12 and is the same thickness as the walls of the tube. It is dimensioned to be an exact fit in the slots 24 on each side of the measurement head. The electrode arrangement when the measurement head is assembled is shown in FIG. 8, which is a cross-sectional view taken through the measuring head vertical centerline along the plane 8—8 indicated in FIG. 2.

The outer electrodes may be connected to conductive stripes 33 as shown in FIG. 9, which is an end view of the conductivity sensor 10. By continuing the conductive stripes 54 along the bottom edge of the electrode assembly substrates 52, an electrical connection may be quickly and easily made after the electrode assemblies are cemented in place by soldering a wire 56 or other electrical connection between the terminal pads 40 on the electrode plate and the conductive stripes 54. The electrical connection would then be cemented to the bottom of the tube and covered by an insulator.

Alternatively, the connection between the outer electrodes and the conductive stripes 33 can be made inside the tube without affecting the operation of the invention. However, making the connection outside the tube avoids the need to perform a soldering or similar operation in the tight confines of the tube and makes for easier inspection of the connection.

In use, a current is passed between one set of the inner or outer electrodes, and the voltage across the other electrodes is measured. Due to the symmetry of the construction, either set of electrodes may be used for the current or the voltage measurement electrodes. The measured calibration factor will be the same for both configurations.

FIG. 10 shows the current flow and electrical field lines when the inner electrodes are used as the measurement electrodes. Current flow is represented by lines 60 running from one outer electrode to the other. Due to the symmetry of the sensor, the current and field lines will be the same, independent of the vertical position in the measuring head.

As shown in FIG. 10, the current density is highest near the ends of the electrode plate 22, and goes to a very low value or zero near the ends 14 and 16 of the measuring head 12. The electrical field is orthogonal to the current flow, and the field lines are shown by lines 62.

Since, as shown in FIG. 10, there is little or no current flow or electrical field outside of the measuring head, the present invention has a negligable sensitivity to the presence of nearby external objects. In order to achieve this, the ends of the measuring head 12 should extend substantially beyond the ends of electrode plate 22. Preferably the distance from the electrode plate 22 to the end of the measuring head 12 ($d_1$ in FIG. 8) should be at least twice the distance between the electrode plate and the side walls of the measuring head ($d_2$ in FIG. 8), and more preferably four times that distance.

Figure 11:
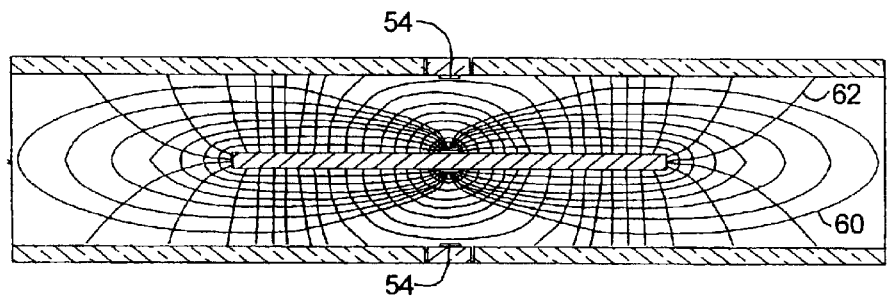
FIG. 11 shows current and field lines when the outer electrodes are used for voltage measurement.

The dimensions of the measuring head are not critical. In the described embodiment, the measuring head is approximately 2"×0.7"×0.3". Other dimensions may be used, either smaller or larger. FIG. 11 shows the current and field lines when the outer electrodes are used as the voltage measuring electrodes. As in FIG. 10, the external current density and electrical field is essentially zero.

As can be seen from FIGS. 10 and 11, with the present invention, the field lines are parallel to the surface of the voltage measuring electrodes in both situations. This is important, since the effects of both electrode contamination and electrode polarization are minimized or eliminated when the field is constant across the entire surface of the electrode.

The configuration and operation of the conductivity sensor described greatly increases the ease of deployment in the typical environment. Since the sensor is immune to the effects of objects that would affect the sensitivity of other conductivity sensors, a sensor may be assembled and calibrated in the laboratory, without the need to calibrate it attached to the instrument housing with which it will be deployed. Since these housings are frequently very much larger than the conductivity sensor, this is a great advantage.

Additionally, the length of the measurement head may be increased to allow antifouling paint to be applied and reapplied to the ends of the tubes, which would affect the calibration of other, prior art sensors. This allows for ease of maintenance in the field.

The embodiment described above utilizes a measurement head which is in the form of a long, rectangular tube. This configuration has the advantage that it is simple and easy to assemble. Other configurations for the measuring head may be used in implementing the present invention, although they may be more difficult to fabricate.

Figure 12:
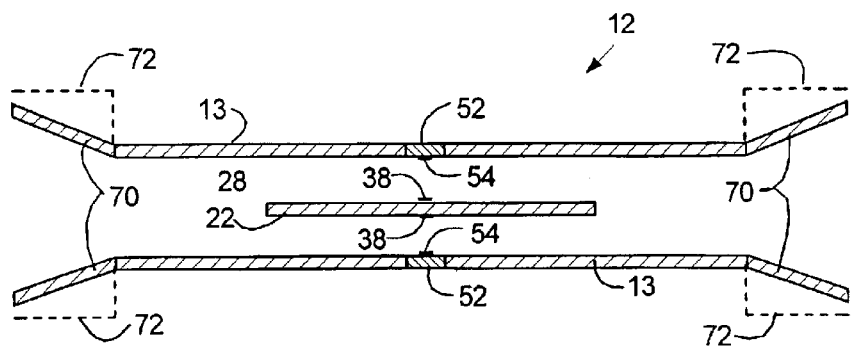
FIG. 12 illustrates alternate configurations of the measuring head.

For example, FIG. 12 is a top view, similar to FIG. 8, illustrating two such alternate configurations. In FIG. 12, the two sidewalls 13 of the measuring head are flared outwardly at both ends, as shown by walls 70. The field line patterns will be similar to those shown in FIGS. 10 and 11, and the advantages discussed above will pertain to this configuration also. Other possible modifications include a measuring tube with a stepped end, illustrated in FIG. 12 by dotted lines 72. Alternatively, the ends could be curved, or they could be angled, stepped, or curved inwardly, although this would inhibit the flushing action through the tube.

The sensor may also be made with an asymmetric cross-section while still achieving the advantage of being insensitive to external objects. For example, the electrode plate 22 could be offset to one side so that it is closer to one of the sidewalls 13 than the other. Asymmetrical configurations may be more sensitive to fouling or other contamination of the electrodes, however, since the field lines will tend to be more curved near one electrode than the other.

There has been described a new and useful conductivity sensor, especially useful for use in oceanographic measurements. While the operation and advantages of the invention have been described with reference to the exemplary embodiments described above, it should be appreciated that modifications to these embodiments will be made by those of ordinary skill in the art in applying the teachings of the invention to different situations and applications. Accordingly, the present invention should not be limited by the embodiments described above, but rather the scope of the invention should be interpreted in accordance with the following claims.

What is claimed is:

1. A conductivity sensor, comprising:
   a hollow tube made of an insulating material and being of uniform cross-section along at least a portion of its length and open at each end;
   a divider plate, made of an insulating material, shorter in length than the tube and located midway along the length of the tube, and which extends completely across the tube so as to divide the tube longitudinally into two equal halves on either side of the plate;
   two inner electrodes respectively located on either side of the divider plate and logitudinally positioned in the center of each side of the plate;
   two outer electrodes, each located inside the tube in one of said halves on the inside wall opposite an inner electrode; and
   terminal means for providing an electrical connection to each of the inner and outer electrodes.

2. The conductivity sensor of claim 1 wherein the distance from the ends of the divider plate to the ends of the tube is greater than twice the distance between the inner and outer electrodes.

3. The conductivity sensor of claim 1 wherein the distance from the ends of the divider plate to the ends of the tube is it at least four times the distance between the inner and outer electrodes.

4. The conductivity sensor of claim 1 where the inner and outer electrodes are in the form of stripes, longer than they are wide, and wherein the stripes are oriented orthogonally to axis of the tube.

5. The conductivity sensor of claim 1 wherein the hollow tube has a rectangular cross-section so that the tube has top and bottom walls and two side walls; and
   wherein the divider plate is in the form of a rectangular wall running lengthwise through the middle of the tube and extending from the top wall of the tube to the bottom wall.

6. The conductivity sensor of claim 5 wherein the outer electrodes comprise two conductive stripes applied to each of the side walls of the tube midway along its length; and wherein the inner electrodes comprise two conductive stripes applied to each side of the divider plate midway along its length.

7. The conductivity sensor of claim 6 wherein the conductive stripes forming the inner and outer electrodes extend from the top wall of the tube to the bottom wall.

8. The conductivity sensor of claim 7 wherein the dimensions of the tube cross-section and the thickness of the divider plate are such that said equal halves on each side of the divider plate are substantially square in cross-section.

9. A conductivity sensor, comprising:
   a hollow rectangular tube of uniform cross-section along its length, having top, bottom, and side walls, and being open on each end;
   a flat electrode plate shorter than the length of the tube, extending from the top wall to the bottom wall of the tube parallel to the side walls, and being located midway between the side walls and midway along the length of the tube;
   two outer electrodes, each comprising vertical stripe formed on the inside of a respective one of the side walls of the tube midway along its length;
   two inner electrodes, each comprising a vertical stripe formed on a respective one of the sides of the electrode plate midway along its length; and
   means for providing electrical connection to each of the electrodes.

10. The conductivity sensor of claim 9 wherein the distance from the ends of the electrode plate to the ends of the tube is greater than twice the distance between the inner and outer electrodes.

11. The conductivity sensor of claim 9 wherein the distance from the ends of the electrode plate to the ends of the tube is it at least four times the distance between the inner and outer electrodes.

12. The conductivity sensor of claim 9 further comprising a slot in the bottom wall of the tube through which the divider plate runs;
    the electrode plate further comprising a support section which extends through said slot so as to project beyond the tube; and
    base means attached to the support section of the divider plate for mounting the conductivity sensor.

13. The conductivity sensor of claim 12 wherein the electrode plate includes two conductive stripes on each side of the support section, the first conductive stripe on each side extending into the tube and forming the inner electrode at its upper end;
    and further comprising means for connecting the second conductive stripe on each side of the electrode plate to the outer electrode on that side.

14. The conductivity sensor of claim 13 wherein each of the outer electrodes is an assembly including a conductive stripe on the surface of a mounting plate; and
    wherein the tube includes a slot on each side for receiving the outer electrode assembly.

15. The conductivity sensor of claim 14 wherein the base means includes a plug adapted to be received by a receptacle in a pressure-tight relationship;
    the block including a slot through which the electrode plate extends; and
    wherein the conductive stripes extend through the slot to provide means for electrical connection to the electrodes from the underside of the plug.

16. A conductivity sensor, comprising:

a hollow tube made of an insulating material, open at each end, and having its length as its largest dimension;

a divider plate, made of an insulating material, shorter in length than the tube and located inside the tube and partway along the length of the tube so that the tube extends beyond the ends of the divider plate, the divider plate extending completely across the tube so as to divide the tube into two sections on either side of the plate;

two inner electrodes respectively located on either side of the divider plate;

two outer electrodes, each located on the inner wall of the tube, each electrode being positioned opposite and across from an inner electrode; and terminal means for providing an electrical connection to each of the inner and outer electrodes.

17. The conductivity sensor of claim 16, wherein the hollow tube is of rectangular cross section along at least a portion of its length.

18. The conductivity sensor of claim 16 wherein the inner and outer electrodes are located midway between the ends of the hollow tube.

19. The conductivity sensor of claim 18 wherein the hollow tube has a symmetrical cross-section, and wherein the divider plate is positioned so as to divide the hollow tube into two equal sections on either side of the plate.

* * * * *